(12) United States Patent
Agrawal et al.

(10) Patent No.: US 7,851,454 B2
(45) Date of Patent: *Dec. 14, 2010

(54) SHORT IMMUNOMODULATORY OLIGONUCLEOTIDES

(75) Inventors: Sudhir Agrawal, Shrewsbury, MA (US); Ekambar R. Kandimalla, Southboro, MA (US); Dong Yu, Westboro, MA (US); Lakshmi Bhagat, Framingham, MA (US)

(73) Assignee: Idera Pharmaceutials, Inc., Cambridge, MA (US)

( * ) Notice: Subject to any disclaimer, the term of this patent is extended or adjusted under 35 U.S.C. 154(b) by 377 days.

This patent is subject to a terminal disclaimer.

(21) Appl. No.: 11/877,767

(22) Filed: Oct. 24, 2007

(65) Prior Publication Data

US 2009/0010938 A1 Jan. 8, 2009

Related U.S. Application Data

(62) Division of application No. 10/361,111, filed on Feb. 7, 2003, now Pat. No. 7,354,907.

(51) Int. Cl.
*A01N 43/04* (2006.01)
*A61K 31/70* (2006.01)
*A61K 39/395* (2006.01)
*A61K 39/00* (2006.01)
*A61K 39/38* (2006.01)
*A61K 39/12* (2006.01)
*A61K 39/002* (2006.01)
*A61K 39/02* (2006.01)
*A61K 39/35* (2006.01)
*A61K 39/36* (2006.01)
*A61K 47/00* (2006.01)

(52) U.S. Cl. .............................. 514/44 R; 514/2; 514/8; 514/12; 424/184.1; 424/234.1; 424/141.1; 424/130.1; 424/278.1; 424/265.1; 424/277.1; 424/275.1; 424/204.1

(58) Field of Classification Search ....................... None
See application file for complete search history.

(56) References Cited

U.S. PATENT DOCUMENTS

| | | | |
|---|---|---|---|
| 5,366,878 A | 11/1994 | Pederson et al. | |
| 5,635,377 A | 6/1997 | Pederson et al. | |
| 5,856,462 A | 1/1999 | Agrawal | |
| 5,968,909 A | 10/1999 | Agrawal et al. | |
| 6,426,334 B1 | 7/2002 | Agrawal et al. | |
| 6,476,000 B1 | 11/2002 | Agrawal et al. | |
| 6,815,429 B2 | 11/2004 | Agrawal | |
| 7,045,609 B2 * | 5/2006 | Metelev et al. | 536/22.1 |
| 7,105,495 B2 * | 9/2006 | Agrawal et al. | 514/44 R |
| 7,115,579 B2 * | 10/2006 | Agrawal et al. | 514/44 A |
| 7,176,296 B2 * | 2/2007 | Agrawal et al. | 536/23.1 |
| 7,255,868 B2 * | 8/2007 | Fearon et al. | 424/280.1 |
| 7,262,286 B2 * | 8/2007 | Kandimalla et al. | 536/23.1 |
| 7,276,489 B2 * | 10/2007 | Agrawal et al. | 514/44 R |
| 7,329,648 B2 * | 2/2008 | Agrawal | 514/44 R |
| 7,354,907 B2 * | 4/2008 | Agrawal et al. | 514/44 A |
| 7,405,285 B2 * | 7/2008 | Agrawal et al. | 536/23.1 |
| 7,407,944 B2 * | 8/2008 | Agrawal et al. | 514/44 R |
| 7,427,405 B2 * | 9/2008 | Agrawal et al. | 424/277.1 |
| 7,470,674 B2 * | 12/2008 | Agrawal et al. | 514/44 R |
| 7,498,425 B2 * | 3/2009 | Agrawal et al. | 536/23.1 |
| 7,498,426 B2 * | 3/2009 | Agrawal et al. | 536/23.1 |
| 7,517,862 B2 * | 4/2009 | Agrawal et al. | 514/44 R |
| 7,566,702 B2 * | 7/2009 | Agrawal et al. | 514/44 R |
| 7,569,554 B2 * | 8/2009 | Kandimalla et al. | 514/44 R |
| 7,595,305 B2 * | 9/2009 | Agrawal et al. | 514/44 R |
| 7,615,539 B2 * | 11/2009 | Uhlmann et al. | 514/44 R |
| 7,632,822 B2 * | 12/2009 | Agrawal et al. | 514/44 R |
| 2002/0151518 A1 | 10/2002 | Agrawal et al. | |
| 2003/0129605 A1 | 7/2003 | Yu et al. | |
| 2004/0097719 A1 | 5/2004 | Agrawal et al. | |
| 2004/0152649 A1 | 8/2004 | Krieg | |
| 2004/0156825 A1 | 8/2004 | Agrawal et al. | |
| 2004/0198685 A1 | 10/2004 | Agrawal et al. | |
| 2004/0266709 A1 | 12/2004 | Kandimalla et al. | |
| 2004/0266710 A1 | 12/2004 | Kandimalla et al. | |
| 2005/0009773 A1 | 1/2005 | Kandimalla et al. | |
| 2005/0026858 A1 | 2/2005 | Kandimalla et al. | |
| 2005/0026861 A1 | 2/2005 | Kandimalla et al. | |
| 2005/0130918 A1 | 6/2005 | Agrawal et al. | |
| 2005/0222072 A1 | 10/2005 | Wang et al. | |

(Continued)

FOREIGN PATENT DOCUMENTS

EP 1393745 A1 3/2004

(Continued)

OTHER PUBLICATIONS

Tokunaga et al, J. Natl. Cancer Inst 72 :955-962 (1984).
Yamamoto et al., Jpn. J. Cancer Res. 79 : 866-873 (1988).
Messina et al., J. Immunol. 147: 1759-1764 (1991).
Tokunaga et al., Microbiol. Immunol. 36: 55-66 (1992).
Yamamoto et al, J. Immunol 148; 4072-4076 (1992).
Krieg et al., Nature 374: 546-549 (1995).
Halpern et al., Cell Immunol., 167: 72-78 (1996).
Klinman et al., Proc. Natl. Acad. Sci. U.S.A. 93: 2879-2883 (1996).
Liang et al., J. Clin. Invest. 98: 1119-1129 (1996).
Sato et al, Science 273: 352-354 (1996).

(Continued)

*Primary Examiner*—N. M Minnifield
(74) *Attorney, Agent, or Firm*—Wood, Phillips, Katz, Clark & Mortimer

(57) ABSTRACT

The invention relates to modulation of the immune system. More particularly, the invention relates to modulating the immune system through the use of oligonucleotide-derived compounds. The invention provides immunostimulatory agents that are less expensive to make than existing immunostimulatory oligonucleotides. The immunostimulatory agents according to the invention can, in preferred embodiments, cause immune stimulation across species lines.

8 Claims, 5 Drawing Sheets

U.S. PATENT DOCUMENTS

| | | | |
|---|---|---|---|
| 2005/0277604 A1* | 12/2005 | Krieg et al. | 514/44 |
| 2006/0014713 A1* | 1/2006 | Agrawal et al. | 514/44 |
| 2006/0019908 A1* | 1/2006 | Mistry et al. | 514/28 |
| 2006/0019909 A1* | 1/2006 | Agrawal et al. | 514/44 |
| 2006/0025365 A1* | 2/2006 | Agrawal et al. | 514/44 |
| 2006/0074040 A1* | 4/2006 | Kandimalla et al. | 514/44 |
| 2006/0094681 A1* | 5/2006 | Agrawal et al. | 514/44 |
| 2006/0135454 A1 | 6/2006 | Kandimalla et al. | |
| 2006/0211641 A1* | 9/2006 | Agrawal et al. | 514/44 |
| 2006/0217328 A1* | 9/2006 | Kandimalla et al. | 514/44 |
| 2006/0287261 A1* | 12/2006 | Agrawal et al. | 514/44 |
| 2006/0287262 A1* | 12/2006 | Agrawal et al. | 514/44 |
| 2007/0072198 A1 | 3/2007 | Kandimalla et al. | |
| 2007/0093439 A1* | 4/2007 | Agrawal et al. | 514/44 |
| 2007/0105800 A1* | 5/2007 | Agrawal et al. | 514/44 |
| 2007/0105801 A1* | 5/2007 | Agrawal et al. | 514/44 |
| 2007/0173469 A1* | 7/2007 | Agrawal et al. | 514/44 |
| 2007/0179103 A1* | 8/2007 | Agrawal et al. | 514/44 |
| 2007/0219153 A1* | 9/2007 | Kandimalla et al. | 514/44 |
| 2008/0027214 A1* | 1/2008 | Kandimalla et al. | 536/23.1 |
| 2008/0152662 A1* | 6/2008 | Agrawal et al. | 424/184.1 |
| 2008/0193437 A1* | 8/2008 | Agrawal et al. | 424/130.1 |
| 2008/0206265 A1 | 8/2008 | Kandimalla et al. | |
| 2008/0279785 A1 | 11/2008 | Kandimalla et al. | |
| 2008/0292648 A1 | 11/2008 | Kandimalla et al. | |
| 2009/0010938 A1* | 1/2009 | Agrawal et al. | 424/141.1 |
| 2009/0053206 A1 | 2/2009 | Kandimalla et al. | |
| 2009/0206265 A1* | 8/2009 | Tomuta et al. | 250/370.08 |

FOREIGN PATENT DOCUMENTS

| | | |
|---|---|---|
| WO | WO 98/49288 A1 | 11/1998 |
| WO | WO 01/12804 A2 | 2/2001 |
| WO | WO 01/55370 A2 | 8/2001 |
| WO | WO 01/83503 A2 | 11/2001 |
| WO | WO 02/26757 A2 | 4/2002 |
| WO | WO 03/057822 A2 | 7/2003 |
| WO | WO 2004/064782 A3 | 8/2004 |
| WO | WO 2007/055682 A2 * | 5/2007 |
| WO | WO 2008/068638 A2 * | 6/2008 |

OTHER PUBLICATIONS

Zhao et al., Antisense Nucleic Acid Drug Dev. 7: 495-502 (1997).

Hartmann et al., J. Immunol 164: 1617-1624 (2000).

Yu et al., "Immunomers—Novel 3'-3'-Linked CpG Oligodeoxyribonucleotides as Potent Immunomodulatory Agents", Nucleic Acids Research, 30(20):4460-4469 (2002).

Yu et al., "Potent CpG Oligonucleotides Containing Phosphodiester Linkages: In Vitro and In Vivo Immunostimulatory Properties", Biochem. And Biophys. Res. Comm., 297:83-90 (2002).

Bhagat et al., "CpG Penta- and Hexaddeoxyrobonucleotides as Potent Immunomodulatory Agents", Biochem. And Biophsy. Res. Comm., 300(4):853-861 (2003).

Kandimalla et al., "Divergent Synthetic Nucleotide Motif Recognition Pattern: Design and Development of Potent Immunomodulatory Oligodeoxyribonucleotide Agents with Distinct Cytokine Induction Profiles", Nuc. Acids. Res., 31(9):2393-2400 (2003).

Li et al., "Oligodeoxynucleotides Containing Synthetic Immunostimulatory Motifs Augment Potent Th 1 Immune Responses to HbsAg in Mice", Int'l. Immunopharmacology, 5:981-991 (2005).

Zhu et al., "Modulation of Ovalbumin-Induced Th2 Response by Second-Generation Immunomodulatory Oligonucleotides in Mice", Int'l. Immunopharmacology, 4:851-862 (2004).

Klinman et al., "Therapeutic Applications of CpG-Containing Oligodeoxynucleotides", Antisense & Nucleic Acid Drug Development, 8:181-184 (1998).

Zhao et al., "Immunostimulatory Activity of CpG Containing Phosphorothioate Oligodeoxynucleotide is Modulated by Modification of a Single Deoxynucleotide", Bioorg. & Med. Chem. Lett., 10:1051-1054 (2000).

Kandimalla et al., "Towards Optimal Design of Second Generation Immunomodulatory Oligonucleotides", Curr. Opin. Mol. Therap., 4(2):122-129 (2002).

Yu et al., "Accessible 5'-End of CpG-Containing Phosphorothioate Oligodeoxynucleotides is Essential for Immunostimulatory Activity", Bioorg. & Med. Chem. Lett., 10:2585-2588 (2000).

Zhao et al., Biochemical Pharmacology, 52/10:1537-1544 (1996).

Marshall et al., "Novel Chimeric Immunomodulatory Compounds Containing Short CpG Oligodeoxyribonucleotides Have Differential Activities in Human Cells", Nucleic Acids Res., 31(17):5122-5133 (2003).

Kandimalla et al., "Conjugation of Ligands at the 5'-End of CpG DNA Affects Immunostimulatory Activity", Biocon. Chem., 13:966-974 (2002).

Kandimalla et al., "A Dinucleotide Motif is Oligonucleotides Shows Potent Immunomodulatory Activity and Overrides Specie-Specific Recognition Observed with CpG Motif", 100(24):14303-14308 (2003).

Klinman et al., Drug News Perspect, 13:289-296 (2000).

Agrawal et al., Current Cancer Drug Targets, 1:197-209 (2001).

McCluskie et al., Vaccine, 19:413-422 (2001).

Yu et al., Bioorganic and Medicinal Chemistry Letters, 11:2263-2267 (2001).

Kandimalla et al., Bioorganic and Medicinal Chemistry, 9:807-813 (2001).

Zhao et al., Bioorganic and Medicinal Chemistry Letters, 9:3453-3458 (1999).

Agrawal et al., Current Opinion in Biotechnology, 6 :12-19 (1995).

McCluskie et al., FEMS Immunology and Medical Microbiology, 32:179-185 (2002).

Yu et al., Bioorganic and Medicinal Chemistry, 9:2803-2808 (2001).

Zhao et al., Biochemical Pharmacology, 51/2:173-182 (1996).

* cited by examiner

SHORT IMMUNOMODULATORY OLIGONUCLEOTIDES

RELATED APPLICATIONS

This application is a divisional of U.S. patent application Ser. No. 10/361,111, filed on Feb. 7, 2003 (Now U.S. Pat. No. 7,354,907), the contents of which are incorporated by reference in its entirety.

BACKGROUND OF THE INVENTION

1. Field of the Invention

The invention relates to modulation of the immune system. More particularly, the invention relates to modulating the immune system through the use of oligonucleotide-derived compounds.

2. Summary of the Related Art

Tokunaga et al, J. Natl. Cancer Inst. 72:955-962 (1984); Messina et al., J. Immunol. 147: 1759-1764 (1991); Krieg et al., Nature 374: 546-549 (1995); Sato et al, Science 273: 352-354 (1996), teach that the presence of CpG dinucleotides in certain sequence contexts in bacterial and synthetic oligodeoxyribonucleotides (CpG DNAs) are known to activate vertebrate innate immune reaction, T-cells and B cells.

Yamamoto et al., Jpn. J. Cancer Res. 79: 866-873 (1988); Halpern et al., Cell Immunol., 167: 72-78 (1996); Klinman et al., Proc. Natl. Acad. Sci. U.S.A. 93: 2879-2883 (1996); Zhao et al., Antisense Nucleic Acid Drug Dev. 7: 495-502 (1997) teach that the activation of immune cells by CpG DNA induces secretion of a number of cytokines, including IFN-γ, IL-12, TNF-α, and IL-6, and stimulates expression of costimulatory surface molecules.

Krieg et al., supra; Yamamoto et al, J. Immunol. 148; 4072-4076 (1992); Tokunaga et al., Microbiol. Immunol. 36: 55-66 (1992); Liang et al., J. Clin. Invest. 98: 1119-1129 (1996); Hartmann et al., J. Immunol. 164: 1617-1624 (2000), teach that the presence of a CpG dinucleotide and the sequences flanking the dinucleotide play a critical role in determining the immunostimulatory activity of DNA, that CpG dinucleotides in palindromic or non-palindromic hexameric sequences ($P_1P_2CGP_3P_4$) are required for immune stimulation, and further, that PuPuCGPyPy and PuTCG motifs optimally activate murine and human immune systems, respectively.

While these findings demonstrate that oligonucleotides are useful as immune stimulating agents, some problems with such use still exist. For example, long oligonucleotides are expensive to make and species specificity of flanking sequences limits the breadth of utility of any given oligonucleotide. There is, therefore, a need for less expensive immunostimulatory agents, and preferably immunostimulatory agents that have cross-species efficacy.

BRIEF SUMMARY OF THE INVENTION

The invention provides immunostimulatory agents that are less expensive to make than existing immunostimulatory oligonucleotides. The immunostimulatory agents according to the invention can, in preferred embodiments, cause immune stimulation across species lines. Surprisingly, the present inventors have discovered that short oligonucleotide-based agents that are linked together with appropriate linkers can be made inexpensively and can be designed to cause immune stimulation in multiple species.

In a first aspect, the invention provides an immunomer comprising two or more oligonucleotide branches linked together and having the structure: $5'-N_npYpRpN_np3'-L_m-3'N_npRpYpN_n-5'$; wherein each N is independently selected from a nucleoside, a nucleoside analog; an arabinonucleoside, or an abasic sugar; each p is independently a natural or modified internucleoside linkage; at least one Y is selected from the group consisting of cytosine, 5-hydroxycytosine, N4-alkyl-cytosine, 4-thiouracil or other non-natural pyrimidine nucleoside or 2-oxo-7-deaza-8-methyl-purine, wherein when the base is 2-oxo-7-deaza-8-methyl-purine, it is covalently bound to the 1'-position of a pentose via the 1 position of the base; at least one R is selected from the group consisting of guanine, 2-amino-6-oxo-7-deazapurine, 2-amino-6-thiopurine, 6-oxopurine, or other non-natural purine nucleoside; L is a non-nucleotidic linker; each $n$ is independently a number from 0-4, provided that neither branch exceeds 6 nucleotides; m is a number from 0-10 and wherein each N may optionally and independently be covalently linked to a non-nucleotidic linker.

DETAILED DESCRIPTION OF THE PREFERRED EMBODIMENTS

Figure 1:
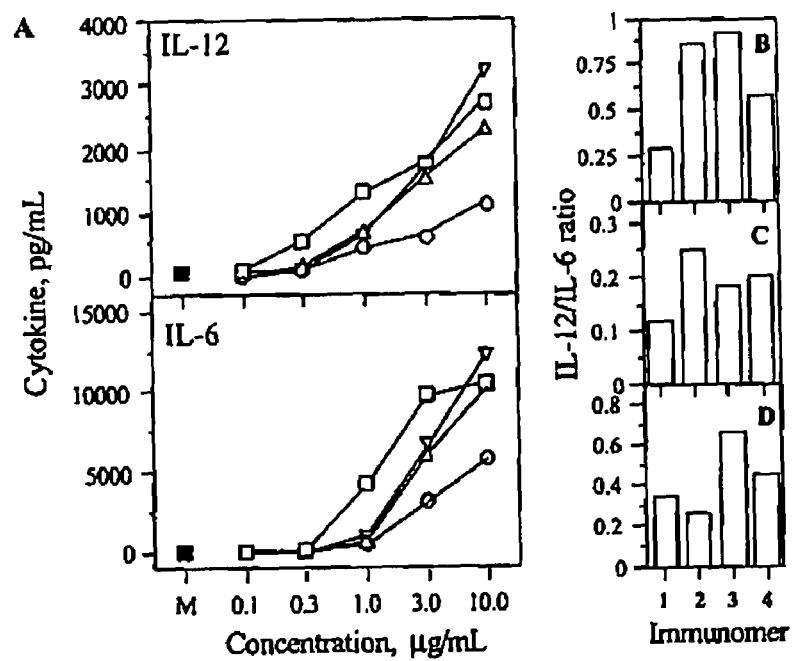
FIG. 1 shows concentration-dependent cytokine induction in BALB/c mouse spleen cell cultures (A) and the ratio of IL-12 to IL-6 induced in BALB/c (B), C57BL/6 (C), and CH3/HeJ (D) mice spleen cell cultures at 3 μg/mL concentration of immunomers, 1 (squares), 2 (circles), 3 (triangles) and 4 (reversed triangles).

The invention relates to modulation of the immune system. More particularly, the invention relates to modulating the immune system through the use of oligonucleotide-derived compounds. The patents and publications cited herein reflect the knowledge of those skilled in the art and are hereby incorporated by reference in their entirety. Any conflict between the teachings of such references and the instant specification shall be resolved in favor of the latter.

The invention provides immunostimulatory agents that are less expensive to make than existing immunostimulatory oligonucleotides. The immunostimulatory agents according to the invention can, in preferred embodiments, cause immune stimulation across species lines. Surprisingly, the present inventors have discovered that short oligonucleotide-based agents that are linked together with appropriate linkers can be made inexpensively and can be designed to cause immune stimulation in multiple species.

In a first aspect, the invention provides an immunomer comprising two or more oligonucleotide branches linked together and having the structure: 5'-$N_n$pYpRp$N_n$p3'-$L_m$-3'$N_n$pRpYp$N_n$-5'; wherein each N is independently selected from a nucleoside, a nucleoside analog; an arabinonucleoside, or an abasic sugar; each p is independently a natural or modified internucleoside linkage; at least one Y is selected from the group consisting of cytosine, 5-hydroxycytosine, N4-alkyl-cytosine, 4-thiouracil or other non-natural pyrimidine nucleoside or 2-oxo-7-deaza-8-methyl-purine, wherein when the base is 2-oxo-7-deaza-8-methyl-purine, it is covalently bound to the 1'-position of a pentose via the 1 position of the base; at least one R is selected from the group consisting of guanine, 2-amino-6-oxo-7-deazapurine, 2-amino-6-thiopurine, 6-oxopurine, or other non-natural purine nucleoside; L is a non-nucleotidic linker; each $_n$ is independently a number from 0-4, provided that neither branch exceeds 6 nucleotides; m is a number from 0-10 and wherein each N may optionally and independently be covalently linked to a non-nucleotidic linker. Preferred internucleoside linkages include phosphodiester, phosphorothioate and methylphosphonate linkages.

For purposes of the invention, a "non-nucleotidic linker" includes, without limitation a linker selected from a linker having a length of from about 2 angstroms to about 200 angstroms, C2-C18 alkyl linker, ethylene glycol linker, poly (ethylene glycol) linker, 2-aminobutyl-1,3-propanediol linker, and branched alkyl linkers, acyclic alkyl linker, cyclic alkyl linker, aryl or heteroaryl linker, heterocyclic linker, polyalcohol linker, peptide linker, lipid linker and carbohydrate linker, each of which may be substituted or non-substituted.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, 2'-deoxypentfuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (Rp)— or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

For purposes of the invention, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

In a second aspect, the invention provides a method for modulating an immune response in a vertebrate. The method according to this aspect of the invention comprises administering to the vertebrate an immunomer according to the first aspect of the invention. For purposes of the invention, the term "vertebrate" includes, without limitation, a fish, bird, or mammal. As used herein, the term "mammal" includes, without limitation rats, mice, cats, dogs, horses, cattle, cows, pigs, rabbits, non-human primates, and humans. "Modulating an immune response" means causing an increase or decrease in, or activation of one or more of B-cell induction, T-cell induction, cytokine induction, natural killer cell induction, specific cell surface marker expression, chemokine induction and activation of antigen presenting cells, such as dendritic cells, monocytes and macrophages.

In a third aspect, the invention provides a method for treating a vertebrate having a disease. The method according to this aspect of the invention comprises administering to the vertebrate an immunomer according to the first aspect of the invention. The term "vertebrate" is as described previously.

In the method according to this aspect of the invention, administration of the immunomer or immunomer conjugate can be by any suitable route, including, without limitation, parenteral, oral, sublingual, transdermal, topical, intranasal, aerosol, intraocular, intratracheal, intrarectal, vaginal, by gene gun, dermal patch or in eye drop or mouthwash form. Administration of the therapeutic compositions of immunomers can be carried out using known procedures at dosages and for periods of time effective to reduce symptoms or surrogate markers of the disease. When administered systemically, the therapeutic composition is preferably administered at a sufficient dosage to attain a blood level of immunomer from about 0.0001 micromolar to about 10 micromolar. For localized administration, much lower concentrations than this may be effective, and much higher concentrations may be tolerated. Preferably, a total dosage of immunomer ranges from about 0.0001 mg per patient per day to about 200 mg per kg body weight per day. It may be desirable to administer simultaneously, or sequentially a therapeutically effective amount of one or more of the therapeutic compositions of the invention to an individual as a single treatment episode.

The following examples are provided to further illustrate certain particularly preferred embodiments of the invention and are not intended to limit the scope of the invention.

Example 1

Synthesis and Purification of Oligomers

CpG DNAs and immunomers were synthesized on a 1 to 2 µmole scale using α-cyanoethylphosphoramidites on a Per-Septive Biosystem's 8990 Expedite DNA synthesizer according to the manufacturer's directions. The phosphoramidites of dA, dG, dC, and T were obtained from PE Biosystems (Foster City, Calif.). C3-linker phosphoramidite was obtained from Glen Research Corporation (Sterling, Va.). Immunomers were synthesized on solid supports carrying DiDMT protected glyceryl linker obtained from ChemGenes (Wilmington, Mass.) using a parallel synthesis. Beaucage reagent (R.I. Chemicals, Orange, Calif.) was used as an oxidant to obtain the phosphorothioate backbone modification. Immunomers were deprotected using standard protocols, purified by HPLC, and dialyzed against USP quality sterile water for irrigation (Braun, Irving, Calif.). The immunomers were lyophilized and dissolved again in distilled water and the concentrations were determined from UV absorbance at 260 nm. All immunomers were characterized by CGE and MALDI-TOF mass spectrometry (Applied Biosystem's Voyager-DE STR Biospectrometry Workstation, Foster City, Calif.) for purity and molecular mass, respectively (Table 1). The purity of full-length immunomers ranged from 89-95% with the rest being shorter by one or two nucleotides (n−1 and n−2) as determined by CGE and/or denaturing PAGE. All CpG DNAs contained less than 0.075 EU/mL of endotoxin as determined by the Limulus assay (Bio-Whittaker, Walkersville, Md.).

TABLE 1

Sequences and chemical modifications of immunomers

| No. | Sequence[a] | Structure[b] | Length[c] | Molecular Weight Found | Molecular Weight Calculated |
|---|---|---|---|---|---|
| 1 | 5'-CTATCTGACGTTCTCTGT-3' |  | 18-mer | 5705 | 5704 |
| 2 | 5'-CTATCTGTCGTTCTCTGT-3' | 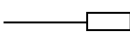 | 18-mer | 5694 | 5695 |
| 3 | 5'-TCGTTG-Y-X-Y-GTTGCT-5' | 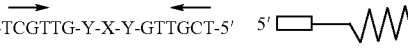 | 6-mer | 4308 | 4313 |
| 4 | 5'-TCGTT-Y-X-Y-TTGCT-5' | 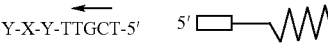 | 5-mer | 3620 | 3623 |
| 5 | 5'-CTGTTG-Y-X-Y-GTTGTC-5' | 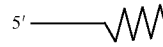 | 6-mer | 4310 | 4313 |

TABLE 1-continued

Sequences and chemical modifications of immunomers

| No. | Sequence[a] | Structure[b] | Length[c] | Molecular Weight Found | Calculated |
|---|---|---|---|---|---|
| 6 | 5'-TCGTTGT-Y-TCGTTGT-3' |  | 15-mer | ND | 4630 |

[a]Arrows indicate 5'→3' directionality of CpG dinucleotide; chemical structures of X and Y linkers are shown below;
[b]Line drawings of immunomer structures, box represents the position of CpG dinucleotide in the sequence, plain and spiked lines represent nucleotide sequence and linker positions, respectively;
[c]length of each segment in immumers excluding linkers.

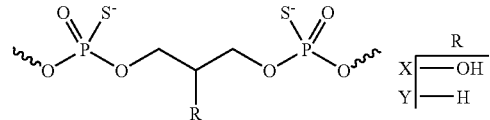

Example 2

Cell Culture Conditions and Reagents

Spleen cells from 4-8 week old BALB/c, C57BL/6 or C3H/HeJ mice were cultured in RPMI complete medium under standard conditions. Murine J774 macrophages (American Type Culture Collection, 10801 University Boulevard, Manassas, Va. 20110-2209) were cultured in Dulbecco's modified Eagles medium supplemented with 10% (v/v) FCS and antibiotics (100 IU/mL of penicillin G/streptomycin). All other culture reagents were purchased from Mediatech (Gaithersburg, Md.).

Example 3

PBMC Isolation from Fresh Murine and Human Blood

Peripheral blood mononuclear cells (PBMCs) from freshly drawn C57BL/6 mouse or healthy human volunteer blood were isolated by Ficoll-Paque density gradient centrifugation method (Histopaque-1077, Sigma, St. Louis, Mo.) under standard conditions.

Example 4

Establishment of Th2 Immune Response in Mice

Four to six week old AKR/J male mice were obtained from Jackson Labs (Bar Harbor, Me.). The mice were given intraperitoneal injections containing 200 μg of conalbumin (Sigma) with ImjectAlum adjuvant (Pierce, Rockford, Ill.) in 100 μL of PBS on days 0, 7, and intranasally challenged on days 14, and 21. The mice were sacrificed 72 hr after the last challenge by $CO_2$ inhalation. Spleens were excised and single cell suspensions were prepared as described above. Spleen cells were treated with immunomers at different concentrations for 2 hr followed by treatment with 50 μg/mL of conalbumin. Supernatants were harvested after 72 hr and IL-5 and IFN-γ levels were measured by ELISA as described below.

Example 5

Cytokine ELISAs

Mouse spleen or J774 cells were plated in 24-well dishes using $5\times10^6$ or $1\times10^6$ cells/mL, respectively. The CpG DNA dissolved in TE buffer (10 mM Tris-HCl, pH 7.5, 1 mM EDTA) was added to a final concentration of 0.03, 0.1, 0.3, 1.0, 3.0, or 10.0 μg/mL to the cell cultures. The cells were then incubated at 37° C. for 24 hr and the supernatants were collected for ELISA assays. The experiments were performed two or three times for each CpG DNA in triplicate for each concentration. The secretion of IL-12 and IL-6 was measured by conventional sandwich ELISA. The required reagents, including cytokine antibodies and standards were purchased from PharMingen (San Jose, Calif.).

Example 6

Mouse Splenomegaly Assay

Female BALB/c mice (4-6 weeks, 19-21 gm) were divided into groups of three mice. CpG DNAs were dissolved in sterile PBS and administered subcutaneosly (SC) to mice at a dose of 5 mg/kg. The mice were sacrificed and the spleens were harvested and weighed.

Example 7

Preparation of J774 Cell Nuclear Extracts and EMSA

NF-κB activation in J774 cells treated with CpG DNAs was carried out and analyzed by conventional EMSA (see e.g., Yu et al., Biochem. Biophys. Res. Commun. 297: 83-90 (2002).

Example 8

Preparation of J774 Cell Lysates and Western Blotting

To detect the phosphorylated and total p38 MAP kinase by Western blotting, J774 cells were grown in serum-reduced medium (0.5% FCS) for 24 hr and then stimulated with immunomers for 30 min. After stimulation, cells were washed with cold PBS and lysed in 2% SDS sample buffer as per the protocol provided by Cell Signaling Technology (Beverly, Mass.). Crude lysates were resolved on 10% SDS polyacrylamide ReadyGels (BioRad, Hercules, Calif.) and blotted onto nitrocellulose membranes. Membranes were probed with a phospho-p38 MAP kinase (Thr 180/Tyr 182) antibody and visualized using enhanced chemiuminescence kit (PE Life Sciences, Boston, Mass.). The blots were then stripped and reprobed with an antibody to p38 MAPK that detects total levels of endogenous p38 MAPK protein. All antibodies were purchased from Cell Signaling Technologies.

Example 9

In Vivo Nude Mice Model and Treatment Plan

The animal use and care protocols were approved by the Institutional Committee on Animal Use and Care of the University of Alabama at Birmingham. Female athymic nude mice (nu/nu, 4-6 weeks old) were obtained from Frederick Cancer Research and Development Center (Frederick, Md., USA) and inoculated with MCF-7 cells. The animals bearing MCF-7 xenograft (50-100 mg) were randomly divided into various treatment groups and treated by subcutaneous injection with short-immunomer 3 at a dose of 0.5 mg/kg or saline (control) on days 1, 3, and 5 every week. The mice were monitored by general clinical observation as well as by body weight and tumor growth. Tumor growth was recorded with the use of calipers, by measuring the long and short diameters of the tumor. Tumor mass (in g) was calculated using the formula $\frac{1}{2} a \times b^2$, where "a" and "b" are the long and short diameters (in cm), respectively.

Example 10

Activity of Short-Immunomers in Murine Spleen Cell and PBMC Cultures

All immunomers showed a concentration-dependent induction of two typical cytokines, IL-12 and IL-6, in BALB/c, C57BL/6, and C3H/HeJ mouse spleen cell cultures. As expected, CpG DNA 1, containing a mouse specific sequence motif, generally showed greater activity than CpG DNA 2 with a human specific sequence motif (Table 2). At lower concentrations, immunomers 3 and 4 generally induced levels of cytokines lying between those found with 1 and 2 in BALB/c mouse cells (FIG. 1). However, at higher concentrations the activities of 3 and 4 matched or exceeded that of 1 even though the short immunomers do not contain the mouse specific 'GACGTT' motif.

Levels of IL-12 and IL-6 induced by 1-5 at concentrations of 3.0 µg/mL in the three strains of mouse spleen cell cultures are shown in Table 2. Levels vary with mouse strain and depend on sequence (1 vs 2) and the structure of the CpG DNA. Control immunomer 5 produced cytokine levels similar to background showing the need for the CpG dinucleotide. In general, a higher IL-12 to IL-6 ratio was found for short-immunomers compared with CpG DNAs 1 and 2 (FIG. 1B). The results obtained in LPS non-responsive strain, C3H/HeJ mouse spleen cell cultures suggest that immunomer activities are not due to LPS contamination acting on the TLR4 receptor.

Previously, we showed that the presence of multiple CpG dinucleotides in oligonucleotides do not increase activity significantly over that due to a single copy. Here, control oligo 6 contains two copies of a CpG containing heptamer joined 5'→3' through a C3-linker. Oligo 6 induced 501±21 pg/mL of IL-12 and 514±164 pg/mL of IL-6 at a concentration of 3.0 µg/mL in C57BL/6 mouse spleen cell culture assays compared with 2833±341 and 2870±760 pg/mL of IL-12, and 24276±4740 and 14256±3304 pg/mL of IL-6 by 1 and 3, respectively, at the same concentration. These results confirm that the activity seen with 3 and 4 is not as a result of the presence of two copies of CpG dinucleotide, but because of their optimal structure for receptor recognition.

In BALB/c mouse bone marrow derived dendritic cell and macrophage cell cultures, short-immunomer 3 induced similar levels of IL-12, IFN-γ, but significantly less IL-6, TNF-α and nitric oxide (NO) compared with CpG DNA 1 (data not shown).

Spleen cells consist of different subsets of cell population than peripheral blood mononuclear cells (PBMCs). To examine whether this difference in cell population could result in different activity, we isolated PBMCs from C3H/HeJ mouse peripheral blood and tested for the ability of short immunomers to induce IL-12 and IL-6 secretion. The results obtained at 10 µg/mL concentration of immunomers are presented in Table 2. Immunomers 3 and 4 showed similar cytokine induction as in spleen cells.

TABLE 2

In vitro cytokine secretion in murine spleen cell, and PBMC cultures and in vivo spleen enlargement

| | | Spleen cell cultures[c] | | | | | | PBMC cultures[d] | |
|---|---|---|---|---|---|---|---|---|---|
| | | BALB/c | | | C57BL/6 | | C3H/HeJ | | C3H/HeJ |
| No. | Spleen Wt. (mg)[b] | IL-12 (pg/mL) | IL-6 (pg/mL) | IL-12 (pg/mL) | IL-6 (pg/mL) | IL-12 (pg/mL) | IL-6 (pg/mL) | IL-12 (pg/mL) | IL-6 (pg/mL) |
| 1 | 153 ± 10.0 | 1775 ± 139 | 9774 ± 798 | 889 ± 71 | 7257 ± 132 | 931 ± 148 | 5465 ± 140 | 6541 ± 254 | 1602 ± 175 |
| 2 | 138 ± 10.3 | 612 ± 6 | 3211 ± 287 | 266 ± 12 | 3605 ± 404 | 157 ± 55 | 2099 ± 234 | 3838 ± 92 | 482 ± 93 |
| 3 | 146 ± 9.7 | 1532 ± 196 | 6086 ± 268 | 831 ± 114 | 11218 ± 631 | 650 ± 89 | 3503 ± 53 | 2327 ± 373 | 1095 ± 106 |
| 4 | 125 ± 9.8 | 1711 ± 126 | 6606 ± 322 | 884 ± 45 | 8410 ± 309 | 783 ± 42 | 3456 ± 307 | 4400 ± 703 | 536 ± 26 |
| 5 | NT | 53 ± 4 | ND | 77 ± 6 | 281 ± 57 | 24 ± 5 | ND | ND | ND |
| M/V[a] | 75 ± 2.4 | 47 ± 1 | 7 ± 1 | 71 ± 12 | 108 ± 38 | 24 ± 6 | 10 ± 3 | 25 ± 8 | 5 ± 3 |

[a]Medium or vehicle (PBS) control;
[b]Average spleen weight of three mice per group obtained after 48 hr of subcutaneous administration of single dose of 5 mg/kg of immunomer;
[c]at a concentration of 3.0 µg/mL of immunomer;
[d]at a concentration of 10.0 µg/mL of immunomer.
NT and ND stand for not tested and not detected, respectively.

Example 11

In Vivo Activity of Short Immunomers as Determined by Increase in Spleen Weight or Splenomegaly To further test the immunostimulatory activity, a single dose of 5 mg/kg of immunomers 1-4 was injected subcutaneously to BALB/c mice, and the spleen weights of mice (3 per group) were measured after 48 hrs [17,32,33]. Average weights of 153, 138, 146 and 125 mg (all±10 mg) were found for 1-4, respectively, while PBS treated controls gave 75±6 mg. Treatment with 6 containing two copies of TCGTTGT gave 123±7 mg after 72 hr recapitulating the lower activity of this compound in cell culture. These results further confirm the immunostimulatory activities found in vitro.

Example 12

Figure 2:
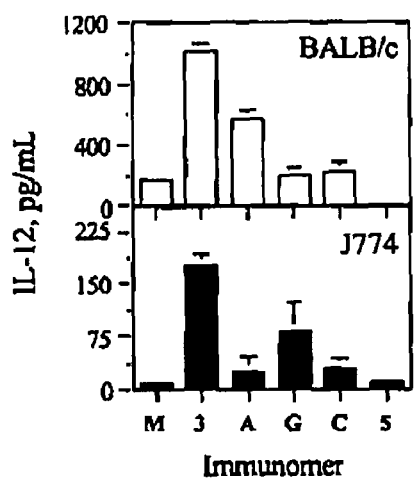
FIG. 2 shows the effect of the nucleotide preceding CpG dinucleotide in short immunomers as determined by the induction of IL-12 secretion in BALB/c mouse spleen and J774 macrophage cell cultures at a concentration of 10.0 μg/mL of immunomers.

Influence of the Nucleotide Preceding CG Dinucleotide on Immunostimulatory Activity Yu et al., Bioorg. Med. Chem. 11: 459-464 (2003) recently showed that the activity of the $P_1P_2CGP_3P_4$ motif containing an abasic deoxynucleoside substitution at $P_1$ is influenced by the nature of the nucleoside (A, C, G, or T) present at $P_2$. Since we completely deleted $P_1$ in short immunomers, we evaluated the effect of different nucleosides at $P_2$. Analogs of 3 were synthesized having A, G, or C, instead of T at each 5'-end. In general, those with A, G, or C showed lower or no induction of cytokines compared to 3 (IL-12 secretion in BALB/c spleen and J774 cell cultures is shown in FIG. 2).

Example 13

Figure 3:
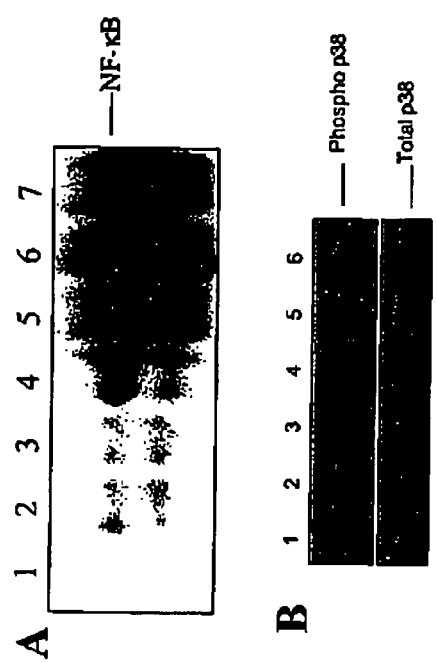
FIG. 3A shows a gel demonstrating activation of NF-κB in J774 macrophages after stimulation for an hour with 10.0 μg/mL of immunomers. lane 1 is media treated control; lane 2 is human specific CpG DNA 2; lane 3 is control non-CpG DNA 5; lane 4 is mouse specific CpG DNA 1; lane 5 is LPS at 0.1 μg/mL; lane 6 is immunomer 3; and lane 7 is immunomer 4.
FIG. 3B shows p38 phosphorylation in J774 macrophages following activation with immunomers for 30 minutes at 10.0 μg/mL concentration. Lane 1 is media treated control; lane 2 is mouse specific CpG DNA 1; lane 3 is immunomer 3; lane 4 is immunomer 4; lane 5 is human specific CpG DNA 2; and lane 6 is LPS at 0.1 μg/mL. Total p38 content is shown in lower panel.

Short-Immunomers Activate NF-κB and p38 Map Kinase Pathways in J774 Cell Cultures Stacey et al., J. Immunol. 157: 2116-2122 (1996) and Yi et al., J. Immunol. 161: 4493-4497 (1998) teach that CpG DNA activates the NF-κB and p38 MAP kinase signaling pathways, which play a critical role in stimulating cytokine gene expression. To see if short immunomers work by the same mechanism, we studied activation of NF-κB in J774 cell nuclear extracts (FIG. 3A). CpG DNA 1, which has a mouse specific sequence, activated NF-κB as expected (lane 4), as did LPS in lane 5 (FIG. 3A). In contrast, CpG DNA 2, containing a human specific sequence, failed to induce NF-κB (lane 2) suggesting specificity of the receptor for the mouse specific CpG DNA sequence. Immunomers 3 and 4, which have two 5'-accessible ends and five-nucleotide homology to the human specific motif, GTCGTT, activated NF-κB (lanes 6 and 7) to the same extent as 1, suggesting that short immunomers are recognized by the mouse receptor.

Additionally, to examine the activation of stress kinase pathways by short immunomers, we examined p38 MAP kinase activity in J774 macrophages after treatment with immunomers (FIG. 3B). Both 3 and 4 activated stress-activated pathways as shown by the presence of phosphorylation product in J774 cell lysates within 30 min of treatment (lanes 3 and 4) as did 1 (lane 2) and LPS (lane 6). In contrast, 2 containing human specific CpG motif failed to activate the stress-activated pathway. Consistent with the activation of NF-κB, 1, 3, and 4, but not 2 and 5, induced IL-12 and IL-6 in J774 cell cultures (data not shown).

Example 14

Immune-Response in Human PBMCs

Figure 4:
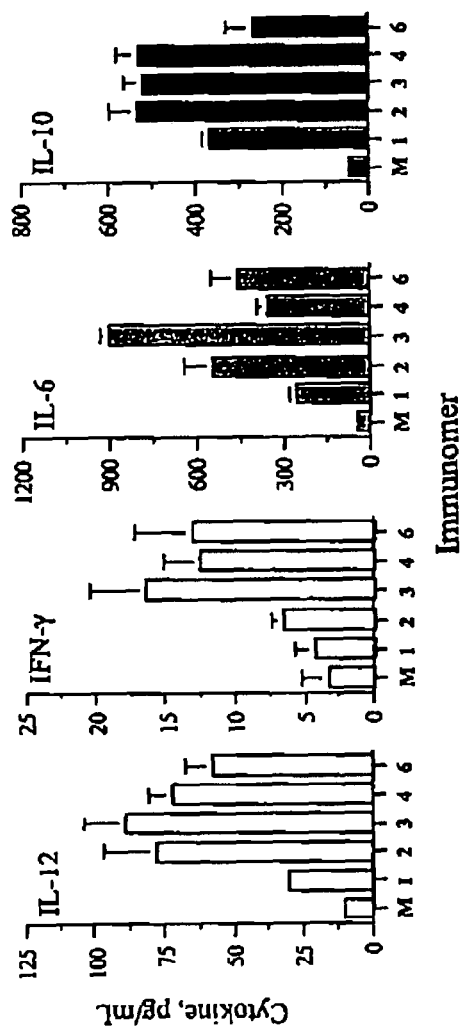
FIG. 4 shows induction of IL12, IFN-γ, IL-6, and IL-10 secretion in human peripheral blood mononuclear cell (hPBMC) cultures at 1.0 μg/mL concentration of short immunomers after 72 hr treatment.

Short-immunomers were further tested for their ability to stimulate human PBMCs to secrete cytokines IL-12, IL-6, IL-10, and IFN-γ. Representative data obtained in a single healthy donor PBMC cultures at 1 µg/mL concentration are shown in FIG. 4. As expected, mouse specific CpG DNA 1 induced lower cytokine production than did human specific 2. Short-immunomers 3 and 4 gave similar or higher levels of cytokine induction than did human specific CpG DNA 2. CpG DNA 6 showed lower cytokine induction than did 2, 3, and 4 despite containing as many CpG dinucleotides as 3 and 4. These results demonstrate that it is the structure of the immunomer and not the number of CpG motifs that effects the immune stimulation.

Example 15

Figure 5:
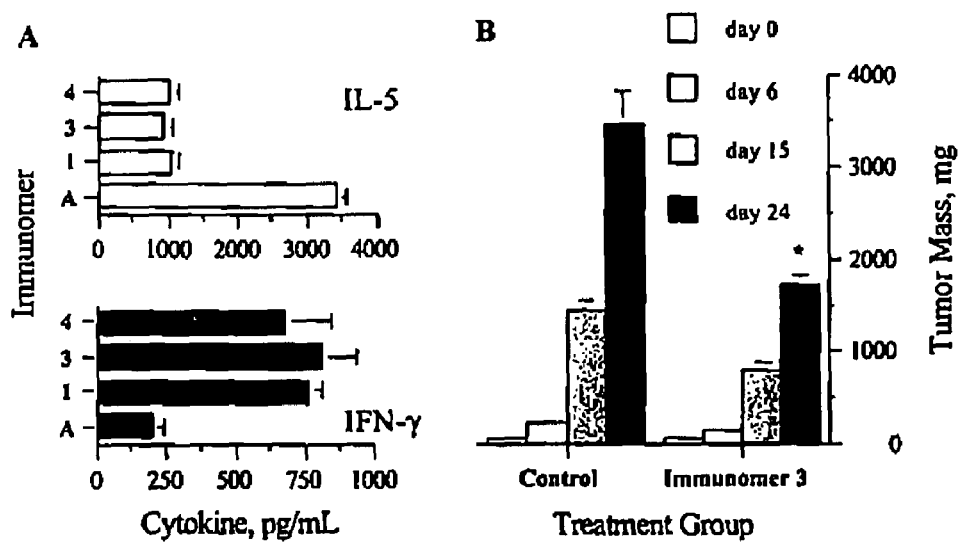
FIG. 5A shows induction of IL-5 (top) and IFN-γ (bottom) secretion in conalbumin-sensitized AKR/J mice spleen cell cultures at 10.0 μg/mL concentration of immunomers. A stands for allergen (conalbumin) senstized but not treated with immunomers.
FIG. 5B shows antitumor activity of immunomer 3 in nude mice bearing MCF-7 human breast cancer xenograft. Control represents the group of mice treated with saline. * Represents statistically significant value (p<0.01).

Effect of Short-Immunomer on IL-5 and IFN-1 Secretion in Allergen-Sensitized Spleen Cell Cultures To assess the effects of treatment of short-immunomers on Th2 cytokines associated with allergic airway responses, we measured IL-5 and IFN-γ secreted in spleen cell cultures obtained from AKR/J mouse challenged with conalbumin. In the absence of immunomer treatment, conalbumin-sensitized spleen cells secreted markedly higher levels of IL-5 and low IFN-γ suggesting predominantly a Th2 type response (FIG. 5A). When the allergen-primed spleen cells were treated with immunomers, a concentration-dependent decrease in IL-5 and increase in IFN-γ secretion was observed. FIG. 5A shows IL-5 (top plot) and IFN-γ (bottom plot) secretion levels at 10 µg/mL concentration of immunomers. These data suggest that short-immunomers not only induce Th1 type cytokine secretion but potently reverse Th2 responses in vitro, and should therefore be useful as a potent adjuvant.

Example 16

Antitumor Activity of Short-Immunomer in Nude Mice Bearing Human Breast Cancer MCF-7 Xenograft To examine if the potential in vitro activity of short-immunomers can be translated in to in vivo antitumor activity, we administered short-immunomer 3 subcutaneously at a dose of 0.5 mg/kg three times a week to nude mice bearing MCF-7 breast cancer xenografts that express wild-type p53. At the relatively low dose, immunomer 3 gave 51% inhibition of MCF-7 tumor growth on day 24 compared with the saline control (p<0.01) (FIG. 5B). These antitumor studies further suggest that short-immunomers exhibit potent antitumor activity in vivo as a result of potent immune stimulation.

What is claimed is:

1. A method for modulating an immune response in a vertebrate, comprising administering to the vertebrate an immunomer comprising two or more oligonucleotide branches linked together and having the structure: 5'-$N_n$pYpRpN$_n$p3'-L$_m$-3'N$_n$pRpYpN$_n$-5'; wherein each N is independently selected from a nucleoside, a nucleoside analog; an arabinonucleoside, or an abasic sugar; each p is independently a natural or modified internucleoside linkage; at least one Y is selected from the group consisting of cytosine, 5-hydroxycytosine, N4-alkyl-cytosine, 4-thiouracil or other non-natural pyrimidine nucleoside or 2-oxo-7-deaza-8-methyl-purine, wherein when the base is 2-oxo-7-deaza-8-methyl-purine, it is covalently bound to the 1'-position of a pentose via the 1 position of the base; at least one R is selected from the group consisting of guanine, 2-amino-6-oxo-7-deazapurine, 2-amino-6-thiopurine, 6-oxopurine, or other non-natural purine nucleoside; L is a non-nucleotidic linker; each $_n$ is independently a number from 0-4, provided that neither branch exceeds 6 nucleotides; m is a number from 0-10 and wherein each N may optionally and independently be covalently linked to a non-nucleotidic linker.

2. The method according to claim 1, wherein the vertebrate is selected from the group consisting of fish, birds, and mammals.

3. The method according to claim 2, wherein the mammal is selected from the group consisting of rats, mice, cats, dogs, horses, cattle, cows, pigs, rabbits, non-human primates, and humans.

4. A method for treating a vertebrate having a disease, comprising administering to the vertebrate an immunomer comprising two or more oligonucleotide branches linked together and having the structure: 5'-$N_n$pYpRpN$_n$p3'-L$_m$-3'N$_n$pRpYpN$_n$-5; wherein each N is independently selected from a nucleoside, a nucleoside analog; an arabinonucleoside, or an abasic sugar; each p is independently a natural or modified internucleoside linkage; at least one Y is selected from the group consisting of cytosine, 5-hydroxycytosine, N4-alkyl-cytosine, 4-thiouracil or other non-natural pyrimidine nucleoside or 2-oxo-7-deaza-8-methyl-purine, wherein when the base is 2-oxo-7-deaza-8-methyl-purine, it is covalently bound to the 1'-position of a pentose via the 1 position of the base; at least one R is selected from the group consisting of guanine, 2-amino-6-oxo-7-deazapurine, 2-amino-6-thiopurine, 6-oxopurine, or other non-natural purine nucleoside; L is a non-nucleotidic linker; each $_n$ is independently a number from 0-4, provided that neither branch exceeds 6 nucleotides; m is a number from 0-10 and wherein each N may optionally and independently be covalently linked to a non-nucleotidic linker.

5. The method according to claim 4, wherein the vertebrate is selected from the group consisting of fish, birds, and mammals.

6. The method according to claim 5, wherein the mammal is selected from the group consisting of rats, mice, cats, dogs, horses, cattle, cows, pigs, rabbits, non-human primates, and humans.

7. The method according to claim 4, wherein the disease to be treated is selected from the group consisting of cancer, an autoimmune disorder, airway inflammation, asthma, allergy, and a disease caused by a pathogen.

8. The method according to claim 4, further comprising administering an agent selected from the group consisting of vaccines, allergens, antigens, antibodies, monoclonal antibodies, chemotherapeutic drugs, antibiotics, lipids, DNA vaccines and adjuvants.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctatctgacg ttctctgt                                                   18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctatctgtcg ttctctgt                                                   18
```